(12) United States Patent
Baets et al.

(10) Patent No.: US 7,244,596 B2
(45) Date of Patent: Jul. 17, 2007

(54) SEPARATION OF BIOMASS FROM LACTIC-ACID CONTAINING FERMENTATION PRODUCTS BY MEANS OF FLOCCULATION

(75) Inventors: Peter Johannes Marie Baets, Gorinchem (NL); Rob Coldenhoff, Arkel (NL)

(73) Assignee: Purac Biochem B.V., Gorinchem (NL)

( * ) Notice: Subject to any disclaimer, the term of this patent is extended or adjusted under 35 U.S.C. 154(b) by 275 days.

(21) Appl. No.: 10/690,548

(22) Filed: Oct. 23, 2003

(65) Prior Publication Data

US 2005/0087497 A1  Apr. 28, 2005

Related U.S. Application Data

(63) Continuation of application No. PCT/NL03/00712, filed on Oct. 22, 2003.

(60) Provisional application No. 60/419,962, filed on Oct. 22, 2002.

(51) Int. Cl.
*C12P 7/62* (2006.01)
*C12P 7/56* (2006.01)
*C12N 1/00* (2006.01)
*B01D 21/01* (2006.01)

(52) U.S. Cl. ............ 435/135; 435/139; 435/243; 210/723

(58) Field of Classification Search ............ 435/135, 435/139, 243; 210/723
See application file for complete search history.

(56) References Cited

U.S. PATENT DOCUMENTS

| 5,453,365 | A | | 9/1995 | Sterzel et al. ............ 435/135 |
|---|---|---|---|---|
| 5,464,760 | A | * | 11/1995 | Tsai et al. .............. 435/139 |
| 5,766,439 | A | | 6/1998 | Eyal et al. ............... 204/524 |
| 6,074,856 | A | * | 6/2000 | Wong et al. ............. 435/139 |
| 6,384,276 | B2 | * | 5/2002 | Dubois et al. ........... 562/589 |
| 6,472,559 | B2 | * | 10/2002 | Baniel et al. ............ 562/580 |
| 6,509,179 | B1 | * | 1/2003 | Veldhuis-Stribos et al. . 435/139 |
| 6,534,679 | B2 | * | 3/2003 | Eyal et al. .............. 562/589 |
| 6,803,217 | B2 | * | 10/2004 | Moore et al. ............ 435/135 |
| 6,902,917 | B1 | * | 6/2005 | Moore et al. ............ 435/135 |
| 2003/0143659 | A1 | * | 7/2003 | Bijl et al. ............... 435/67 |
| 2005/0124052 | A1 | * | 6/2005 | Moore et al. ............ 435/138 |

FOREIGN PATENT DOCUMENTS

| JP | 59127499 | | 6/1984 |
|---|---|---|---|
| JP | 361028396 | * | 2/1986 |
| WO | WO 98/37050 | | 8/1998 |
| WO | WO 98/58072 | | 12/1998 |

OTHER PUBLICATIONS

J. Hughes et al., Improved Separation of Bacteria With a Dual Flocculant Hydrocol™ System, Biotechnology Techniques, vol. 4, No. 4, pp. 233-236 (1990).

* cited by examiner

*Primary Examiner*—Herbert J. Lilling
(74) *Attorney, Agent, or Firm*—Gilberto M. Villacorta; Sunit Talapatra; Foley & Lardner LLP

(57) ABSTRACT

The present invention is in the field of the preparation of lactic acid by means of fermentation, more particularly it is directed to processes to separate the biomass from the lactic acid-containing fermentation product by means of flocculation.

We have found that for the separation of biomass from lactate and lactic acid-containing fermentation broth the following process is very convenient and suitable;
  a) Subjecting the fermentation broth to an alkalifying step,
  b) adding one or more flocculants, and
  c) separating the biomass flocs from the lactate and lactic acid-containing fermentation broth.

With this process even bacteria-based fermentation broths can be suitably handled efficiently and economically.

11 Claims, 1 Drawing Sheet

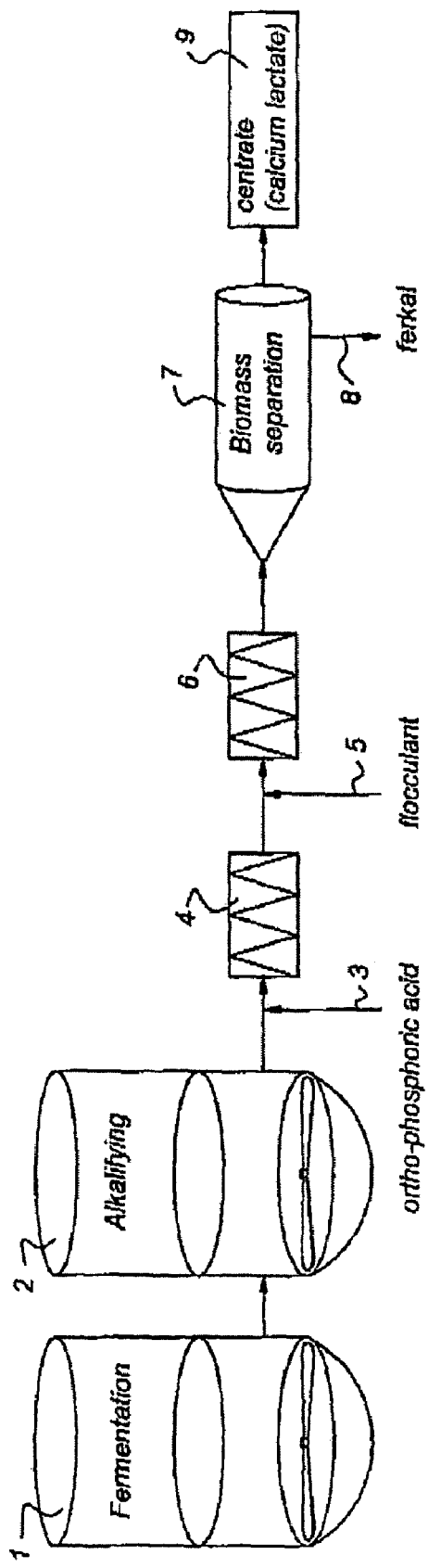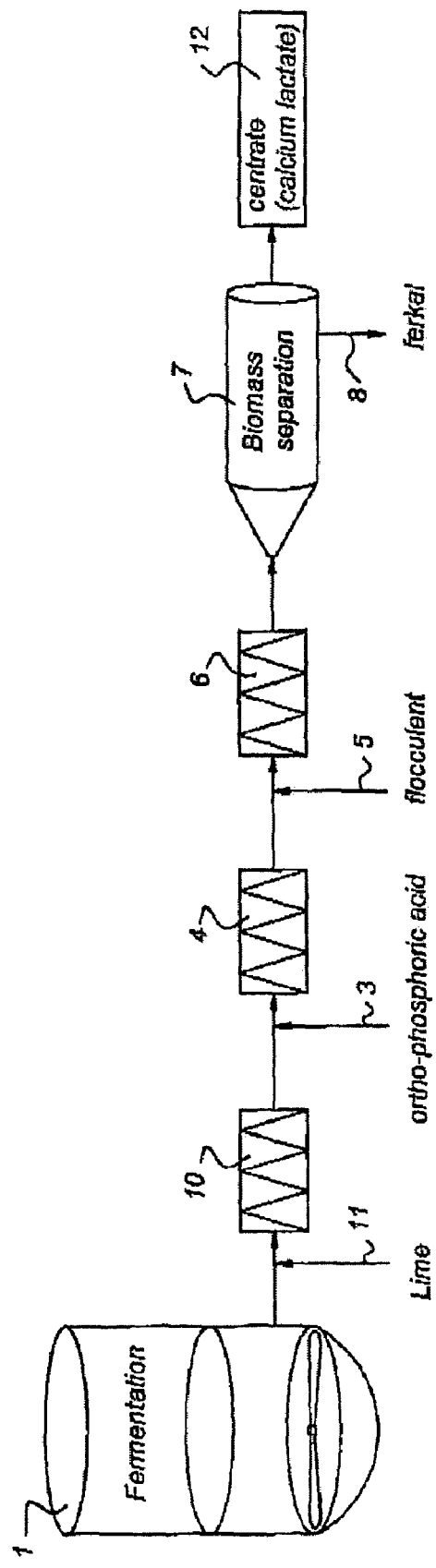

SEPARATION OF BIOMASS FROM LACTIC-ACID CONTAINING FERMENTATION PRODUCTS BY MEANS OF FLOCCULATION

CROSS REFERENCE TO RELATED APPLICATIONS

This application is a continuation of International Application Number PCT/NL2003/000712, filed Oct. 22, 2003, entitled "SEPARATION OF BIOMASS FROM LACTIC-ACID CONTAINING FERMENTATION PRODUCTS BY MEANS OF FLOCCULATION," co-inventors of which are Peter Johannes Marie BAETS and Rob COLDENHOF, which names Purac Biochem B. V. as the Applicant, and which claims the benefit of the priority date of U.S. Provisional Application No. 60/419,962, filed on Oct. 22, 2002. The disclosures of both applications are hereby incorporated herein by reference in their entirety.

FIELD OF THE INVENTION

The present invention is in the field of the preparation of lactic acid by means of fermentation. More particularly, it is directed to processes to separate the biomass from the lactate and lactic acid-containing fermentation product by means of flocculation.

BACKGROUND OF THE INVENTION

Lactic acid, its salts, and esters have long been used as food additives and in various chemical and pharmaceutical applications. More recently, lactic acid has been used as a replacement for present plastic materials in the making of biodegradable polymers as well as in various other new uses where biodegradability is needed or desired, such as for medical implants and slow-release drugs. Accordingly, there is an ever-increasing demand for improved and economically viable lactic acid production processes. The present invention provides substantial improvements over conventional lactic acid production processes that employ fermentation.

The production of lactic acid is commonly carried out using fermentation by means of micro-organisms such as bacteria, yeasts and fungi. The fermentation substrate consists of carbohydrates together with suitable mineral and proteinaceous nutrients. After fermentation, the lactate and lactic acid-containing fermentation products must be separated from the biomass. These lactic acid-containing fermentation products are in the liquid form (i.e., liquid or in solution). Usually the biomass is separated from the lactate and lactic acid-containing fermentation products by means of filtration, centrifuging, flocculation, coagulation, flotation, or combinations thereof. Such a conventional process is described in WO 01/38283, wherein a continuous process for the preparation of lactic acid by means of fermentation is described. When the fermentation is carried out using bacteria, biomass separation is particularly difficult. Because of the small solid particles in the biomass, filtration per se is not possible.

In U.S. Pat. No. 5,453,365 the pH of a calcium or magnesium lactate fermentation broth is increased by means of ammonia and carbon dioxide addition in order to form ammonium lactate and cause precipitation of calcium carbonate or magnesium carbonate. The cellular material is adsorbed on the calcium carbonate or magnesium carbonate and for the most part precipitated therewith. The solids are subsequently separated by means of a filter or centrifuge.

WO 98/58072 describes the flocculation of biological material from organic acid-containing systems, more particularly ammonium acrylate systems. Flocculation here is caused by the addition of an anionic particulate material.

In U.S. Pat. No. 5,766,439 a method is described for biomass removal by microfiltration.

SUMMARY OF THE INVENTION

The present invention is directed to a process for the separation of biomass from lactate and lactic acid-containing fermentation product present in a fermentation broth by subjecting the fermentation broth to an alkalifying step, adding one or more flocculants, and separating the biomass flocs from the lactate and lactic acid-containing fermentation broth. In some embodiments of the present invention, in the alkalifying step the pH of the fermentation broth is increased to above 9 and is more preferably increased to above 10. In some embodiments of the present invention, the mixture obtained in the alkalifying step is aged at a temperature between 25–100° C. for a period of time up to 1000 hours. In a preferred embodiment, the ageing time is above 8 hours.

In some embodiments of the present invention, the alkalifying residence time is between 1 second and 4 hours. In a preferred embodiment, the alkalifying residence time is between 1 second and 15 minutes.

The process of the present invention may be carried out wherein the flocculant is orthophosphoric acid. In a preferred embodiment, the flocculant is a polymeric flocculant.

The process of the present invention may be carried out wherein steps a) and b) are conducted with agitation, wherein steps a) and b) are combined, wherein the alkalifying step is conducted in-line, and/or wherein step b) is conducted in-line.

The process of the present invention may also be carried out wherein the biomass precipitate is subjected to one or more washing steps and one or more additional alkalifying and/or flocculant addition steps, followed by separation of the biomass precipitate.

Further, the present invention contemplates a clarified lactate and lactic acid-containing broth prepared by any of the processes as described above, the processes including the separation of biomass from a lactate and lactic acid-containing fermentation product present in a fermentation broth by subjecting the fermentation broth to an alkalifying step, adding one or more flocculants, and separating the biomass flocs from the lactate and lactic acid-containing fermentation broth. This embodiment may be carried out wherein in the alkalifying step the pH of the fermentation broth is increased to above 9, preferably above 10, wherein the mixture obtained in the alkalifying step is aged at a temperature between 25–100° C. for a period of time up to 1000 hours, wherein the aging time is above 8 hours and up to 1000 hours, wherein the alkalifying step is conducted in-line and wherein the alkalifying residence time is between 1 second and 4 hours, and/or with any other process steps as described herein.

Even further, the present invention includes lactic acid purified from a clarified lactate and lactic acid-containing broth prepared by any of the above processes, said processes including the separation of biomass from a lactate and lactic acid-containing fermentation product present in a fermentation broth by subjecting the fermentation broth to an alkalifying step; adding one or more flocculants; separating the biomass flocs from the lactate and lactic acid-containing fermentation broth; and further including purifying the lactic acid from the lactate and lactic acid-containing fermentation broth. This embodiment may be carried out wherein in the alkalifying step the pH of the fermentation broth is increased to 9, preferably above 10, wherein the mixture obtained in the alkalifying step is aged at a temperature between 25–100° C. for a period of time up to 1000 hours, wherein the aging time is above 8 hours and up to 1000 hours, wherein the alkalifying step is conducted in-line and wherein the alkalifying residence time is between 1 second and 4 hours, and/or with any other process steps as described herein.

BRIEF DESCRIPTION OF THE DRAWINGS

FIG. 1 shows a flow chart of one embodiment of the present invention.

FIG. 2 shows a flow chart of another embodiment of the present invention.

DETAILED DESCRIPTION OF THE INVENTION

We have found that, for the separation of biomass from lactate and lactic acid-containing fermentation broth, the following flocculation process is very convenient and suitable:
a) Subjecting the fermentation broth to an alkalifying step,
b) adding one or more flocculants, and
c) separating the biomass flocs from the lactate and lactic acid-containing fermentation broth.

With this process even bacteria-based fermentation broths can be suitably handled efficiently and economically.

In step a), the pH of the fermentation broth is increased in at least one alkalifying step to above 9 and preferably above 10. Said alkalifying step is performed maintaining the temperature of the fermentation broth between 25–100° C.; temperatures of 60–80° C. are preferred. This pH increase may be obtained by adding alkaline compounds either as solids, in solution, or in suspension. Examples of suitable alkaline compounds include calcium (hydr)oxide, sodium hydroxide, potassium hydroxide, lithium hydroxide, magnesium (hydr)oxide, ammonium compounds such as ammonium hydroxide and quaternary ammonium hydroxides, and amines such as mono ethanolamine, diethanolamine, triethanolamine, polyethylene-imines (PEI's), modified PEI's, and the like, to the fermentation broth. The use of calcium (hydr)oxide is preferred because it ensures a lactic acid-containing product of high clarity.

Optionally, the mixture obtained in the one or more alkalifying steps is aged at a temperature between 25–100° C. for up to 1000 hours. When an ageing step is used, the ageing time is preferably above 8 hours; this ageing time ensures proper flocculation and low metal and silica concentration in the lactic acid-containing fermentation product.

It was found, surprisingly, that omitting the ageing step altogether and controlling the alkalifying residence time to very short periods gave extremely good results. The "alkalifying residence time" is defined as the time between increasing the pH to above 9, preferably above 10, and separating out the biomass flocs. When setting the alkalifying residence time to between 1 second and 4 hours, it was found that proper flocculation was ensured, the amount of polysaccharide in the final lactate and lactic acid-containing fermentation product was very low, and the final lactate and lactic acid-containing fermentation product had a very high clarity. Even better results were obtained when setting the alkalifying residence time to between 1 second and 15 minutes. This has advantages because the subsequent steps for the purification of the lactic acid may be less stringent or may even be omitted, thus saving time and money. If used, subsequent purification steps may include distillation, including short path distillation and vacuum distillation, crystallisation, electrodialysis, extraction, carbon treatment, ion exchange and combinations thereof.

In order to ensure a very short alkalifying residence time, the one or more alkalifying steps are preferably conducted in-line. With in-line alkalifying, residence times between 1 and 60 seconds may be reached. To increase the residence time, for instance up to 15 minutes, additional vessels may be used.

Suitable flocculants are known in the art and need no further elucidation here. In the process according to the present invention, the use of orthophosphoric acid and/or polymer flocculant, such as anionic polyacrylic amides and copolymers thereof or acrylates, is preferred. Other suitable polymeric filocculants are described in Kirk-Othmer, *Encyclopedia of Chemical Technology* $3^{rd}$ *ed*, Volume 10, pages 489–523. Usually, about 50 to 500 ppm orthophosphoric acid is used, based on the total weight of the fermentation broth; preferably, about 100–300 ppm is used. The amount of polymer may range from 1–2000 ppm, preferably between 10–500 ppm, and more preferably between 20–200 ppm. Also, combinations of flocculants may be used, with a combination of orthophosphoric acid and polymeric flocculant being preferred. During the addition of the flocculants, a fermentation broth temperature of between 25–100° C., preferably between 60–80° C., is maintained. In order to control the alkalifying residence time properly, it is preferred to add the flocculants in-line. The order of addition of the various flocculants is not critical and any order of addition may be used. According to the present invention, the preferred order of addition is: (i) alkaline material, (ii) orthophosphoric acid, and (iii) polymeric flocculant. The flocculants are usually added in solution, the concentration of the solution being adapted to obtain the desired viscosity.

Both steps a) and b) are preferably conducted with agitation. The agitation, however, should not be so severe as to break up the biomass flocs. Said agitation may be accomplished with static mixers, pumps, and the like. Steps a) and b) may also be combined.

The separation of the biomass flocs from the lactate and lactic acid-containing fermentation broth may be done with any liquid-solid separation method, such as filtration (for instance with a bed filter, drum filter, rotating vacuum filter, or belt filter), or sedimentation (for example with a static sedimentation tank, sedimentation centrifuge or a cyclone). These separation methods are known in the art and need no further elucidation here.

Optionally, the biomass precipitate is washed once or more times after separation and subjected to one or more additional flocculant addition steps, followed by separation of the biomass precipitate to increase the overall process lactic acid yield. The conditions (shear, temperature) of the wash step are carefully selected to ensure that a maximum amount of lactate and lactic acid is being washed out, while a maximum amount of polysaccharides present in the biomass precipitate is retained in the biomass.

EXAMPLES

The invention is further illustrated by means of the following examples, which are not to be construed as being limiting.

Example 1

A process setup for biomass removal consisting of an alkalifying vessel and an inline ortho-phosphoric acid and flocculant dosing mechanism according to FIG. 1 was used. In this setup, sugar free fermentation broth with a temperature of 70° C., obtained from bacterial fermentation using lactic acid-producing bacteria, was pumped into the alkalifying vessel. In this vessel, a 25% calcium hydroxide suspension was added to the broth. After being alkaline for 6–7 hours, the broth was transferred in the direction of the decanter and meanwhile mixed with 160 ppm orthophosphoric acid (OPA) and 60 ppm polymeric flocculant, an anionic polyacrylic amide, inline. In the decanter, the broth is easily split into biomass and lactic acid-containing fermentation product, hereinafter referred to as Product 1.

Example 2

A process setup for biomass removal consisting of an alkalifying vessel and an inline ortho-phosphoric acid and flocculaut dosing mechanism according to FIG. 1 was used. In this setup, sugar free fermentation broth with a temperature of 70° C., obtained from bacterial fermentation using lactic acid-producing bacteria, was pumped into the alkalifying vessel. In this vessel, a 25% calcium hydroxide suspension was added to the broth. Being alkaline for 1 hour, the broth was transferred in the direction of the decanter and meanwhile was mixed with 160 ppm orthophosphoric acid (OPA) and 60 ppm polymeric flocculant, an anionic polyacrylic amide, inline. In the decanter the broth is easily split into biomass and lactic acid-containing fermentation product, hereinafter referred to as Product 2.

Example 3

A process set-up for biomass removal consisting of an alkalifying vessel and an inline orthophosphoric acid and flocculant dosing mechanism according to FIG. 1 was used. In this setup, sugar free fermentation broth with a temperature of 70° C., obtained from bacterial fermentation using lactic acid-producing bacteria, was pumped into the alkalifying vessel. In this vessel, a 25% calcium hydroxide suspension was added to the broth. Being alkaline for 16 hours, the broth was transferred in the direction of the decanter and meanwhile was mixed with 160 ppm orthophosphoric acid (OPA) and 60 ppm polymeric flocculant, an anionic polyacrylic amide, inline. In the decanter, the broth is easily split into biomass and lactic acid-containing fermentation product, hereinafter referred to as Product 3.

Example 4

In this example, a setup was used according to FIG. 2. In this embodiment, the alkalifying vessel is skipped and an extra static mixer is implemented. A 25% calcium hydroxide suspension was dosed inline. After dosing, the fermentation broth obtained from bacterial fermentation using lactic acid producing bacteria was mixed with a static mixer. Just after this static mixer, 160 ppm orthophosphoric acid was added and the flow was mixed again. To the mixed broth a solution of polymeric flocculant, 60 ppm anionic polyacrylic amide, was added and this was again mixed inline using a static mixer. Sulzer SMI-W DN25 static mixers were used in each case. The alkalifying residence time was about 15 seconds. Passing this mixer, the flow entered the decanter. In the decanter it is split into biomass and lactate and lactic acid-containing fermentation product, hereinafter referred to as Product 4.

When comparing the polysaccharide contents in Products 1, 2, 3 and 4, Products 2, 3 and 4 have a polysaccharide content of about 50% of the polysaccharide content of the Product 1. The metal content (especially Fe) of Products 1 and 3 was lower than that of Products 2 and 4. All products were clear, with Product 4 having a very high clarity.

While the invention has been described in connection with specific embodiments thereof, it will be understood that it is capable of further modifications and this application is intended to cover any variations, modifications, uses, or adaptations of the invention following, in general, the principles of the invention and including such departures from the present disclosure as come within known or customary practice within the art to which the invention pertains and as may be applied to the essential features herein before set forth and as follows in the scope of the appended claims. All publications, internet information from disclosed websites, and patent documents cited in this application are incorporated by reference in their entirety for all purposes to the same extent as if each individual publication or patent document where so individually denoted.

The invention claimed is:

1. A process for the separation of biomass from lactate and lactic acid-containing fermentation product present in a fermentation broth by:
   a) subjecting the fermentation broth to an alkalifying step;
   b) adding one or more flocculants; and
   c) separating the biomass flocs from the lactate and lactic acid-containing fermentation broth, wherein the fermentation broth is subjected to an alkaline residence time of between 1 second and 15 minutes or above 8 hours, the alkaline residence time being the time between increasing the pH to above 10 and separating the biomass flocs.

2. The process according to claim 1, wherein the mixture obtained in the alkalifying step is aged at a temperature between 25–100° C. for a period of time up to 1000 hours.

3. The process according to claim 1, wherein the aging time is above 8 hours.

4. The process according to claim 1, wherein the alkalifying residence time is between 1 second and 15 minutes.

5. The process according to claim 1, wherein the flocculant is orthophosphoric acid.

6. The process according to claim 1, wherein the flocculant is a polymeric flocculant.

7. The process according to claim 1, wherein steps a) and b) are conducted with agitation.

8. The process according to claim 1, wherein steps a) and b) are combined.

9. The process according to claim 1, wherein the alkalifying step is conducted in-line.

10. The process according to claim 1, wherein step b) is conducted in-line.

11. The process according to claim 1, wherein the biomass precipitate is subjected to one or more washing steps and one or more additional alkalifying and/or flocculant addition steps, followed by separation of the biomass precipitate.

* * * * *